(12) United States Patent
Schu et al.

(10) Patent No.: US 6,389,315 B1
(45) Date of Patent: May 14, 2002

(54) IMPLANTABLE MEDICAL DEVICE INCORPORATING SELF-TIMED LOGIC

(75) Inventors: Carl A. Schu, Plymouth; Daniel R. Greeninger, Coon Rapids; David L. Thompson, Fridley, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/513,044

(22) Filed: Feb. 25, 2000

(51) Int. Cl.⁷ .............................................. G61N 1/362
(52) U.S. Cl. ...................................................... 607/16
(58) Field of Search .............................. 607/1, 2, 9, 16, 607/4, 5

(56) References Cited

U.S. PATENT DOCUMENTS

| | | | |
|---|---|---|---|
| 4,515,159 A | * 5/1985 | McDonald et al. | 607/9 |
| 5,014,057 A | 5/1991 | Mintzer | 341/161 |
| 5,186,169 A | 2/1993 | Schaldach | |
| 5,305,463 A | 4/1994 | Fant et al. | 395/800 |
| 5,655,090 A | 8/1997 | Weingart | 395/800.25 |
| 5,752,070 A | 5/1998 | Martin et al. | |
| 5,822,609 A | 10/1998 | Richter | 395/800.35 |
| 5,986,466 A | 11/1999 | Sobelman et al. | 326/39 |

FOREIGN PATENT DOCUMENTS

| | | | |
|---|---|---|---|
| EP | 0 911 061 A2 | 4/1999 | A61N/1/36 |
| GB | 2 330 673 A | 4/1999 | G06F/9/2238 |
| GB | 2 335 293 A | 9/1999 | G06F/1/32 |

OTHER PUBLICATIONS

"Clockless Logic Overview," @ http://www.sanders.com/hpc/CL/Overview.html (9/97).
A Fully Asynchronous Digital Signal Processor Using Self–Timed Circuits, *IEEE Journal of Solid–State Circuits*, vol. 25, No. 6, 12/90, pp. 1526–1536.
Fant et al. in "NULL Convention Logic™" (Theseus Logic, Inc., 1997, 35 pp.)
Wang et al. in "Technology Independent Design Using NULL Convention Logic™" (Theseus Logic, inc., Oct. 19, 1998 19 pp.).
Cogency Technology, @ http//:www.cogency.co.uk/tech/index.html, © 1999, 8 pp.

* cited by examiner

*Primary Examiner*—George R. Evanisko
(74) *Attorney, Agent, or Firm*—Girma Wolde-Michael

(57) ABSTRACT

Improved operating system architecture for an implantable medical device incorporating self-timed logic for reducing power consumption and increasing and improving processing capabilities is disclosed. The self-timed logic is employed to implement digital signal processors (DSPs) including analog to digital (ADC) signal converters, a state machine or the components of microprocessor cores, e.g., the CPU, arithmetic logic units (ALU), on-chip RAM and ROM and data and control buses, and other logic units, e.g., additional RAM and ROM, a direct memory address (DMA) controller, a block mover/reader, a cyclic redundancy code (CRC) calculator, and certain uplink and downlink telemetry signal processing stages. The self-timed CMOS logic is incorporated into the same IC or ICs with clocked CMOS logic in a manner that minimizes the size of the clock tree serving the clocked CMOS logic, allows for efficient allocation of chip real estate, and provides manufacturing economies.

11 Claims, 4 Drawing Sheets

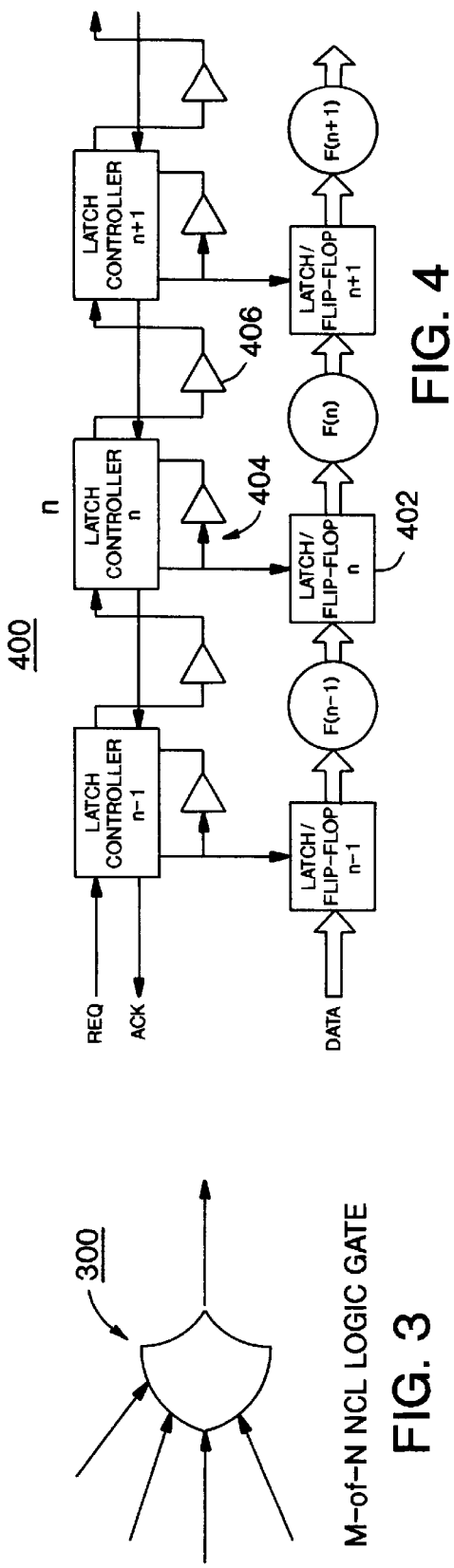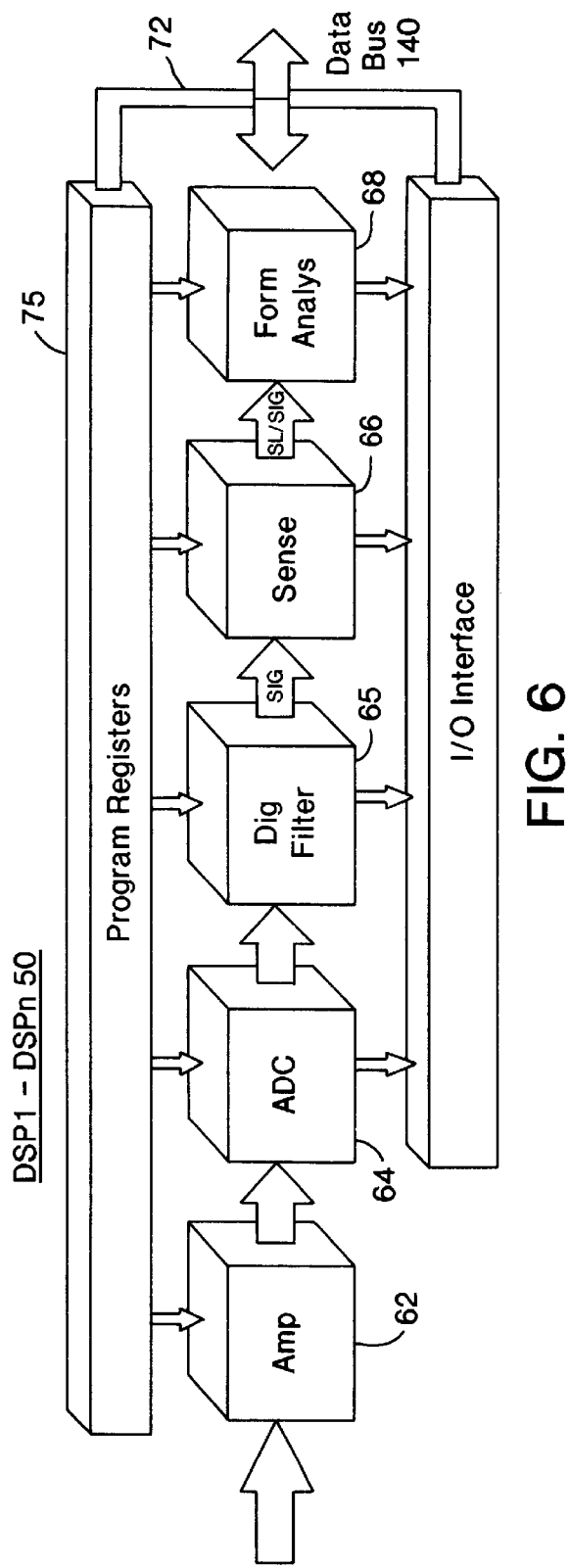

IMPLANTABLE MEDICAL DEVICE INCORPORATING SELF-TIMED LOGIC

REFERENCE TO RELATED APPLICATION

Reference is hereby made to commonly assigned U.S. patent application Ser. No. (P-9202.00) filed on even date herewith for IMPLANTABLE MEDICAL DEVICE INCORPORATING ADIABATIC CLOCKED LOGIC and to U.S. patent application Ser. No. 09/467,288 filed on Dec. 20, 1999, for POWER DISSIPATION REDUCTION IN MEDICAL DEVICES USING ADIABATIC LOGIC.

FIELD OF THE INVENTION

This invention relates generally to implantable medical devices, and more particularly to an improved operating system architecture incorporating self-timed logic for reducing power consumption and increasing and improving processing capabilities.

BACKGROUND OF THE INVENTION

A wide variety of implantable medical devices (IMDs) that employ electronic circuitry for providing electrical stimulation of body tissue and/or monitoring a physiologic condition are known in the art. A number of IMDs of various types are known in the art for delivering electrical stimulating pulses to selected body tissue and typically comprise an implantable pulse generator (IPG) for generating the stimulating pulses under prescribed conditions and at least one lead bearing a stimulation electrode for delivering the stimulating pulses to the selected tissue. For example, cardiac pacemakers and implantable cardioverter/defibrillators (ICDs) have been developed for maintaining a desired heart rate during episodes of bradycardia or for applying cardioversion or defibrillation therapies to the heart upon detection of malignant tachyarrhythmias. Other IMDs have been developed for applying electrical stimulation or other therapies, e.g., drugs, to nerves, the brain, muscle groups and other organs and body tissues for treating a variety of conditions.

Over the past 40 years, such IMDs have evolved from relatively bulky, crude, and short-lived devices providing simple stimulation therapies and monitoring functions to complex, long-lived, and miniaturized IMDs, e.g., cardiac IMDs providing a wide variety of pacing and/or cardioversion and defibrillation therapies and/or monitoring functions. Numerous other programmable functions have been incorporated including enhanced capacity to detect and discriminate cardiac arrhythmias, to store data and to uplink telemetry data related to arrhythmia episodes and applied therapies (if any). Moreover, the capability of interrogating stored device data and initiating real time uplink telemetry of physiologic data, e.g. the real time cardiac EGM and blood pressure and the like, have been incorporated into such IMDs.

The earliest implantable pacemaker IPGs employed very simple analog circuit oscillators formed by discrete transistors and other circuit components and were very short-lived and electrically inefficient. Integrated circuit (IC) technology and battery improvements were made that enabled hermetic sealing of IMD housings, improved reliability and lengthened the operating life of the IMD. The MEDTRONIC® SPECTRAX® pacemaker IPGs incorporated an analog IC with digital IC into a digital clocked logic operating system architecture providing an array of sophisticated operating functions, programmability of operating modes and parameters, data storage, and uplink telemetry functions. Successive generations of IMDs of this type have incorporated increased operating modes and functions through further improvements in circuitry and long-lived, low current output, low voltage batteries. Most recently, a wide number of IMD system architectures have been developed that incorporate custom microcomputers comprising a microprocessor, RAM and ROM, bus, and related elements of a typical microcomputer and other control logic, memory, input signal processing circuitry and therapy delivery output circuitry. The complexity of the circuitry, the functions provided, the longevity, and the reliability of the IMDs have all increased dramatically while the IMD size has decreased.

Current IMD operating system architectures typically are embodied in two or more ICs and discrete components mounted to one (or more) substrate employing hybrid fabrication circuitry techniques. Certain of the ICs or circuitry on a particular IC perform analog functions, input signal processing, and output therapy delivery. Digital logic ICs or circuitry are formed employing complementary metal oxide semiconductor (CMOS) fabrication technology. The digital logic ICs perform signal processing, timing, and state change functions embodying Boolean logic timed synchronously by a system-wide, clock, and are referred to herein as "clocked logic" ICs or circuits.

The power consumption of CMOS circuits consists generally of two power consumption factors, namely "dynamic" power consumption and "static" power consumption. The static power consumption is only due to current leakage, as the quiescent current of such circuits is zero. Dynamic power consumption is due to the current required to charge internal and load capacitances during switching, i.e., the charging and discharging of such capacitances, and is the dominant form of power consumption for CMOS technology. The dynamic power (P) for the CMOS circuit is a function of nodal capacitance (C), the clock or switching frequency (F), and the supply voltage ($V_{DD}$) in accordance with the formula $P = C V_{DD}^2 F$.

In accordance with this formula for dynamic power (P) consumption, efforts have been made conventionally in CMOS IC designs to scale down the supply voltage for an entire device (e.g., a hybrid or IC) to provide the minimally required power to reliably operate all of the clocked logic of the device. For example, in the Medtronic SYMBIOS® pacemaker IPGs, the logic circuitry was powered by a voltage regulator controlling the IC supply voltage to a "sum of thresholds" supply. This regulator provided a supply to the IC (i.e., $V_{DD}$) of several hundred millivolts above the sum of the n-channel and p-channel thresholds of the CMOS transistors making up the IC. This regulator was self calibrating regarding manufacturing variations of the transistor thresholds. This same approach of specifying a high enough voltage to account for fabrication variances is followed even when only a single such CMOS IC is employed in the IMD system. Therefore, in practice, excessive power may be consumed by the CMOS IC or ICs of the IMD operating system.

Other IMDs have reduced power consumption in other varied manners, e.g., by shutting down analog blocks and/or shutting off clocks to logic blocks not being used at particular times. In commonly assigned U.S. Pat. No. 5,916,237, it is proposed that the power delivered to selected sections of the digital logic circuitry in IMDs be cycled between power ON and power OFF states to reduce static power consumption. In many applications, most of the digital logic circuitry may be turned off at various times during each system clock cycle, which reduces static power consumption and average power consumption of the digital clocked logic circuitry.

In addition, microprocessor based IMDs provided by virtually all pacemaker and ICD manufacturers have historically used a "burst clock" design to perform processing operations at a relatively high clock rate (e.g., generally 500–1000 KHz) for relatively short periods of time to gain the benefit of a "duty cycle" to reduce average current drain. A much lower frequency clock (e.g., generally 32 KHz) is used for other timing and control circuitry and/or the processor when not in the high clock rate, burst clock mode. A few illustrative examples which describe the use of a burst clock are provided in U.S. Pat. Nos. 4,561,442, 5,022,395, 5,154,170, and 5,388,578.

Even with these improvements, clocked logic CMOS circuits assembled from logic gates, flip-flops, and other Boolean logic blocks used in IMD system architectures suffer from several limitations and disadvantages. It is necessary to route clock distribution over the complete IC chip area as a clock tree of discrete electrical conductors or lines to reach all clocked logic. The clock tree takes up IC chip real estate that could be used to increase device functions or memory capacity, dissipates power as heat, and increases overall power drain of the IC, decreasing useful life of the IMD battery. Complex timing analysis and worst case design analysis and simulation are required in clocked logic circuits to ensure design integrity because of possible clock skew and the resultant timing errors induced by race conditions. Consequently, it would be desirable to minimize the use of IC real estate occupied by the clock tree, to simplify design analysis and simulation of the IMD system architecture and to decrease power consumption.

For a time, early, large scale and relatively primitive, general purpose computers did not rely upon clocked logic or CMOS circuitry, and instead operated asynchronously. However, clocked computer system architectures replaced the early asynchronous architectures, and computer clock speeds have steadily increased. Increasing the speed at which a digital logic device transitions between logic states, commonly referred to as switching speed, has long been a primary motivation behind many advancements in the semiconductor arts to increase computing and signal processing power. Increasing the switching speed of a clocked logic circuit, however, results in a proportional increase of the dynamic power (P) consumed by the circuitry as it switches more frequently between logic states as described above. The dynamic power (P) is dissipated as heat in high clock rate microprocessors employed in personal computers, necessitating cooling fans and large scale heat sinks to avoid destructive heat buildup.

In recent years, a variety of self-timed or asynchronous logic schemes have been devised in the effort to reduce the reliance upon high speed clocks in very high speed clocked logic circuits used in computing and telecommunications devices. Self-timed or asynchronous logic systems have therefore been proposed to eliminate or minimized clock trees in such high speed ICs for these applications.

Computing power requirements in IMDs have also increased dramatically in recent years while circuitry, batteries and other components have been decreased in size to achieve small sized, long-lived IMDs favored by physicians and patients. It is desirable to continue to reduce size and power consumption and increase and improve processing capabilities of such IMDs.

SUMMARY OF THE INVENTION

In accordance with the present invention, self-timed logic, alternatively called clockless logic or asynchronous logic, is used in lieu of clocked logic in IMD system architectures embodied in a single IC or two or more ICs. Preferably, the self-timed logic implements digital signal processors (DSPs) including analog to digital (ADC) signal converters, a state machine or the components of microprocessor cores, e.g., the CPU, arithmetic logic units (ALU), on-chip RAM and ROM and data and control buses, and other logic units, e.g., additional RAM and ROM, a direct memory address (DMA) controller, a block mover/reader, a cyclic redundancy code (CRC) calculator, and certain uplink and downlink telemetry signal processing stages.

Furthermore, the self-timed CMOS logic can be incorporated into the same IC or ICs with clocked CMOS logic in a manner that minimizes the size of the clock tree serving the clocked CMOS logic allows for efficient allocation of chip real estate, and provides manufacturing economies.

The use of self-timed logic with clocked logic in IMD ICs advantageously reduces dynamic power consumption and dissipation in the remaining clock tree. The diminution of the clock tree makes IC chip real estate available to incorporate further clocked and self-timed logic therein to increase RAM or to add further IMD functional operations. The decrease in dynamic power consumption and the available real estate enables the addition of further features to the IMD operating system while maintaining a desired battery lifetime. The use of self-timed logic circuits reduces complex timing analysis and worst case design analysis and simulation significantly. In certain IMDs, the crystal oscillator, system clock, and clock trees can be eliminated altogether.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 3 is a schematic illustration of a first form of self-timed logic;

FIG. 4 is a schematic illustration of a second form of self-timed logic;

FIG. 6 is a detailed block diagram of a DSP embodied in self-timed logic elements employed for physiologic input signal processing.

DETAILED DESCRIPTION OF THE PREFERRED EMBODIMENTS OF THE INVENTION

The preferred embodiments of the present invention disclose uses of self-timed logic circuits in preference to clocked logic circuits in IMD system architectures where it is possible to do so. Generally speaking, in accordance with the present invention, functions that depend upon precise time-out of fixed or variable time periods are implemented using clocked logic, and functions that are not critically time-dependent, such as computations performed by the microcomputer based control system, are implemented in self-timed logic. Generally, time-dependent functions performed by IMDs involve time periods in the range between 0.1 milliseconds to hours, days or weeks, and a relatively low basic clock speed is used for such timing in the present invention using clock driven timers. But, it is also contemplated that dependence upon clock based timers can be reduced by employing event or signal triggered local timers or "oneshots" in the manner described in commonly assigned U.S. Pat. Nos. 5,391,188 and 5,292,342 to time out certain intervals independently of any clock signal.

Figure 1:
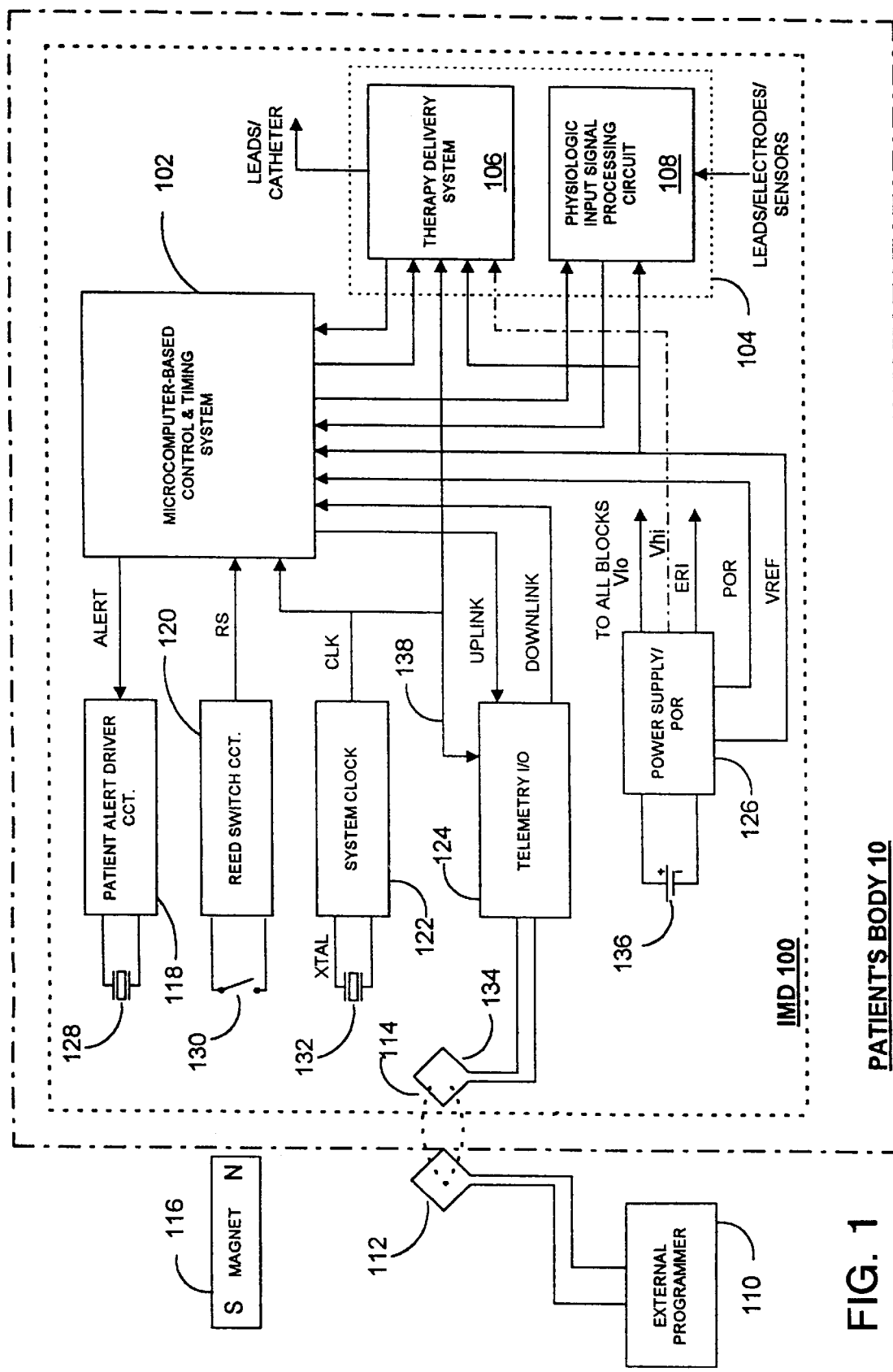
FIG. 1 s a block diagram of a system architecture of an exemplary IMD that incorporates delivery of a therapy and/or physiologic input signal processing in which clocked logic and self-timed logic are incorporated in accordance with the present invention.

FIG. 1 depicts a system architecture of an exemplary IMD 100 implanted into a patient's body 10 that provides delivery of a therapy and/or physiologic input signal processing in which clocked logic and self-timed logic are selectively incorporated in accordance with the present invention. The typical IMD 100 has a system architecture that is constructed about a microcomputer-based control and timing system 102 which varies in sophistication and complexity depending upon the type and functional features incorporated therein. The functions of microcomputer-based IMD control and timing system 102 are controlled by firmware and programmed software algorithms stored in RAM and ROM including PROM and EEPROM and are carried out using a CPU, ALU, etc., of a typical microprocessor core architecture. The microcomputer-based IMD control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. In accordance with the present invention, the reliance upon a clock signal is minimized to similarly minimize the clock tree.

It will also be understood that control and timing of IMD 100 can be accomplished with dedicated circuit hardware as described, for example, in the above-referenced '188 and '342 patents, or state machine logic rather than a programmed micro-computer. A state machine can advantageously be implemented in self-timed logic to perform state transitions asynchronously.

The IMD 100 also typically includes patient interface circuitry 104 for receiving signals from sensors or electrodes located at specific sites of a patient's body 10 and/or delivering a therapy to a site of the patient's body. The typical patient interface circuitry 104 therefore comprises a therapy delivery system 106 and/or a physiologic input signal processing circuit 108 or simply one or the other.

The physiologic input signal processing circuit 108 is coupled to electrodes and/or physiologic sensors on or in the housing of the IMD 100 or situated at sites distanced from the IMD housing, typically in distal portions of elongated leads. In the latter case, physiologic signals developed by such sensors or traversing the electrodes are coupled by way of elongated leads or catheters or transmitted through the body to physiologic input signal processing circuit 108. In accordance with one aspect of the present invention, the physiologic input signal processing circuit 108 is formed of self-timed logic circuitry.

The IMD 100 can comprise an implantable cardiac monitor without a therapy delivery system 106, e.g., an implantable EGM monitor for recording the cardiac electrogram from electrodes remote from the heart as disclosed in commonly assigned U.S. Pat. No. 5,331,966 and PCT publication WO 98/02209. Or the IMD 100 can comprise an implantable hemodynamic monitor (IHM) for recording cardiac electrogram and other physiologic sensor derived signals, e.g., one or more of blood pressure, blood gases, temperature, electrical impedance of the heart and/or chest, and patient activity. The Medtronic® REVEAL® Insertable Loop Recorder having spaced housing EGM electrodes is an example of the former, and the Medtronic® CHRONICLE® IHM coupled with a capacitive pressure and temperature sensing lead and EGM sense electrodes of the type described in commonly assigned U.S. Pat. No. 5,564,434 is an example of the latter.

In these monitor embodiments, physiologic data, e.g., the cardiac EGM and/or sensor derived data is typically stored in RAM in microcomputer-based control and timing system 102 for uplink telemetry to an external programmer 110 when the IMD 100 receives a downlink telemetered interrogation command from the programmer 110. The data storage is either triggered by a timer of the IMD 100 on a periodic basis or by detection logic within the physiologic input signal processing circuit 108 upon satisfaction of certain event detection criteria. In some cases, the patient is provided with a magnet 116 or simplified external programmer 110 that can be applied over the subcutaneously implanted IMD 100 to trigger physiologic data storage when the patient experiences certain symptoms. In either case, event related data, e.g., the date and time, may be stored along with the stored episode data for uplink telemetry in a later interrogation session.

Therapy delivery IMDs 100 include the therapy delivery system 106 that can take a variety of forms and typically involve delivering electrical stimulation to body muscle groups, the heart, the brain, other organs, selected nerves, and the spinal column or the delivery of drugs into organs for therapeutic treatment or into the spinal column for pain relief. It will be understood that most of these therapy delivery IMDs also have a physiologic input signal processing circuit 108 that processes physiologic signals that are used to trigger or modulate therapy delivery and are stored as physiologic signal data for later retrieval as described above.

With respect to therapy delivery device configurations, the IMD 100 and therapy delivery system 106 may be configured to operate an implantable heart assist device or pump implanted in patients awaiting a heart transplant operation. In this case, derived relative blood pressure and/or temperature values may be used to modulate the action of the pump to maintain adequate cardiac output. The IMD 100 and therapy delivery system 106 may also be configured as a cardiomyostimulator to stimulate a muscle surgically wrapped about the heart in synchrony with cardiac depolarizations to increase cardiac output of a diseased heart.

The IMD 100 and therapy delivery system 106 may be configured to include a substance delivery apparatus or pump which is coupled to a suitable catheter extending to a site of the patient's body to deliver a substance, e.g., a therapeutic or diagnostic agent or drug, from a substance reservoir. For example, a drug to treat hypertension may be delivered to the patient's heart or vascular system, or an analgesic may be delivered to the spinal column to relieve intractable pain.

Or IMD 100 may be configured as a cardiac stimulator for sensing cardiac signals and delivering pacing pulses or cardioversion/defibrillation shocks to the heart through therapy delivery system 106. The IMD 100 may include any one or a combination of an anti-tachycardia pacer, anti-bradycardia pacer, cardioverter and/or defibrillator having suitable leads and electrodes extending to the patient's heart as part of the IMD therapy delivery system 106.

Similarly, the IMD 100 and therapy delivery system 106 may be configured with appropriate lead borne electrodes as a deep brain stimulator to control Parkinson's disease, or as a spinal column stimulator or nerve stimulator to control pain. The IMD and therapy delivery system 106 may be configured with appropriate electrodes and/or sensors to detect cardiac ischemia and provide compensatory autonomous nerve stimulation.

The IMD 100, therapy delivery system 106, and physiologic input signal processing circuit 108 may also be configured as a cochlear implant responding to sensor sound transducer inputs and providing stimulation to the cochlea.

These are merely exemplary configurations of IMD 100, therapy delivery system 106, and physiologic input signal processing circuit 108 for therapy delivery and/or monitoring. In all cases, the microcomputer-based control and timing system 102 governs all operating functions employing an appropriate, programmable operating algorithm. FIG. 1 also depicts other typical components common to an IMD 100 in any of these therapy delivery and/or monitoring configurations.

For example, most such IMDs have programmable operating modes and parameters that are stored in RAM in the microcomputer-based control and timing system 102. The operating modes and parameter values can be remotely programmed using the external programmer 110 to transmit commands and values in a downlink telemetry link 114 between external telemetry antenna 112 and IMD telemetry antenna 134 and received and decoded in the telemetry I/O circuit 124 in a manner well known in the art. The application of a magnetic field to a field responsive IMD switch 130, e.g., a reed switch or MAGFET, to provide a telemetry control signal RS from the reed switch circuit 120 is also typically required in current programming and interrogation protocols to enable communications between IMD 100 and external programmer 110. The above-referenced '188 and '342 patents disclose an alternative programming protocol that simply employs the magnet 116 and a MAGFET employed as the IMD switch 130 to make programming changes in a low cost pacing system architecture. Other telemetry protocols have been disclosed that operate at a greater distance between the antennae 112 and 134 and do not rely upon the magnetic field induced closure of the IMD switch 130.

All current IMDs rely upon a source of electrical energy to power the IMD operating system including the circuitry of IMD 100 and to power any electromechanical devices, e.g., valves, pumps, etc. of a substance delivery IMD or to provide electrical stimulation energy of an ICD shock generator, cardiac pacing pulse generator or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF power, current sources, an elective replacement indicator (ERI) signal, and, in the case of an ICD, high voltage power Vhi to the therapy delivery system 106. Not all of the conventional interconnections of these voltages and signals are shown in FIG. 1.

In addition, in certain IMDs, an audible patient alert warning or message is generated by a transducer 128 when driven by a patient alert driver 118 to advise of device operations, battery power level or a monitored patient condition. In ICDs, the patient may be warned of the detection of a malignant tachyarrhythmia and the imminent delivery of a cardioversion/defibrillation shock to enable the patient to assume a resting position prior to delivery.

Figure 5:
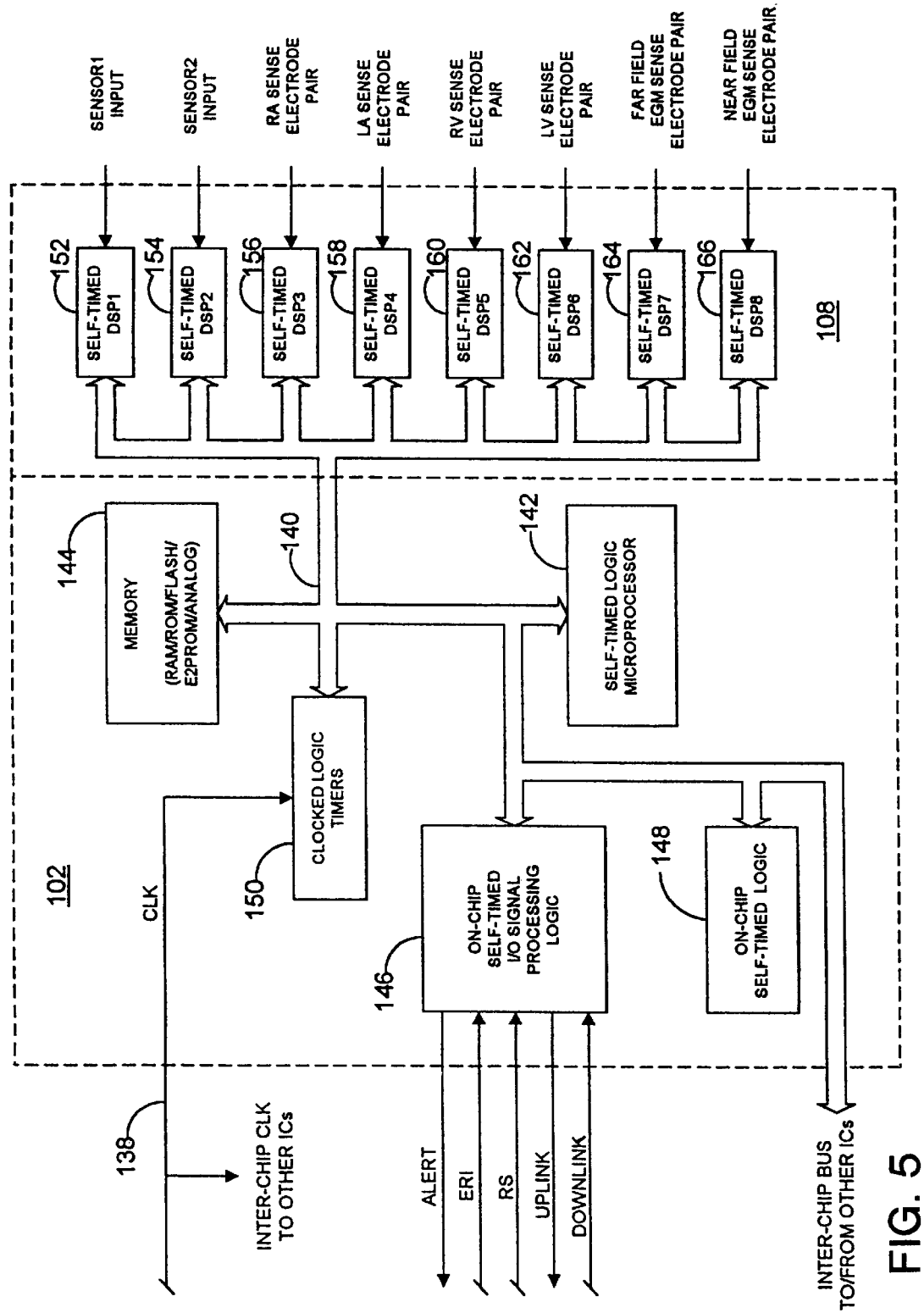
FIG. 5 is a detailed block diagram of the microcomputer-based control and timing system and physiologic input signal processing circuit of FIG. 1 for a multi-chamber pacing system.

Virtually all current electronic IMDs are fabricated as described employing clocked logic ICs that requires a clock signal CLK provided by a piezoelectric crystal 132 and system clock 122 coupled thereto. In FIG. 1, each CLK signal generated by system clock 122 is routed to all applicable clocked logic via a clock tree 138. The system clock 122 provides one or more fixed frequency CLK signal that is independent of the battery voltage over an operating battery voltage range for system timing and control functions. The CLK signal(s) output by the system clock 122 represents at least one and possibly a plurality of differing frequency clock signals that are employed in certain instances in the therapy delivery system 106, in clocked timers of the microcomputer-based control and timing system 102, and in formatting uplink telemetry signal transmissions in the telemetry I/O circuit 124. All logic gates of the clocked logic circuits are preferably switched in state within one clock cycle. Self-timed logic and other unclocked logic may be employed in other parts of therapy delivery system 106, the microcomputer-based control and timing system 102, and in certain downlink telemetry signal reception and decoding stages in the telemetry I/O circuit 124. A minimized clock tree 138 is depicted in FIGS. 2 and 5 for the limited purposes of operating certain clocked timers 150 for certain IMDs, e.g., complex pacing systems as described below.

The incorporation of a system clock 122, clock tree 138, and clocked timers 150 and any other clocked logic may be eliminated entirely if the IMD 100 is configured strictly as a monitor mimicking the functions of the aforementioned Medtronic® REVEAL® Insertable Loop Recorder and CHRONICLE® IHM coupled with a capacitive pressure and temperature sensing lead and EGM sense electrodes and data storage is triggered by the patient. Or, the IMD 100 could be configured as a therapy delivery device with therapy initiated by patient action, e.g., by use of the magnet 116 to close reed switch 130, and with or without contemporaneous storage of physiologic data. In this case, the system clock 122, clock tree 138, and clocked timers 150 and any other clocked logic may be eliminated entirely from the IMD 100. FIG. 1 thus depicts a number of components of exemplary IMD system architectures in which the present invention may be implemented to minimize clocked logic, the associated power drain, and the accompanying necessity of an extensive clock tree 138. It will be understood that other circuit blocks may be included in the exemplary IMD system.

Figure 2:
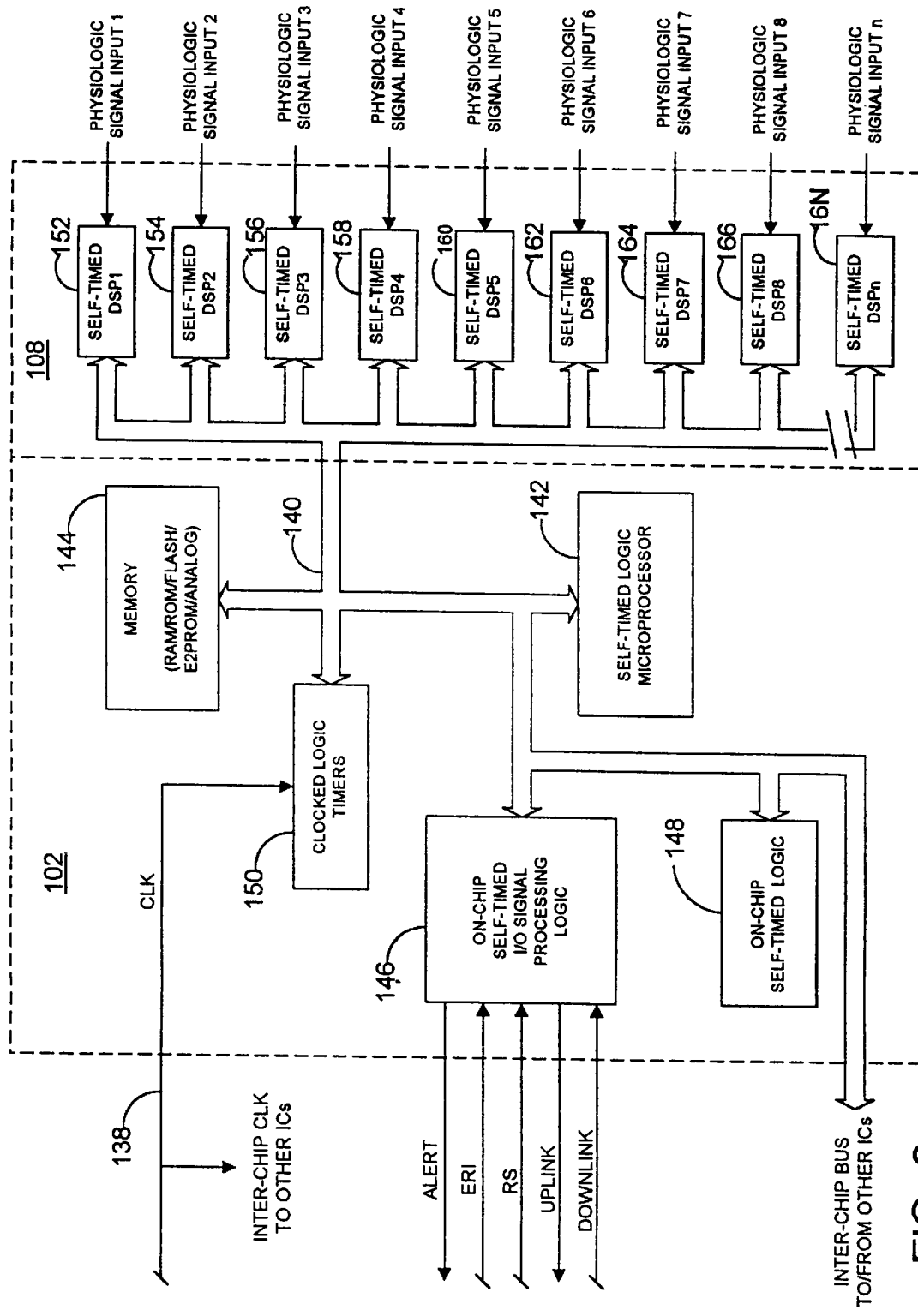
FIG. 2 is a detailed block diagram of the microcomputer-based control and timing system and physiologic input signal processing circuit of FIG. 1 for an exemplary IMD.

FIG. 2 depicts the microcomputer-based control and timing system 102 and physiologic input signal processing circuit 108 of FIG. 1 for an exemplary IMD 100 in greater detail. The microcomputer-based control and timing system 102 and physiologic input signal processing circuit 108 are formed on a single IC. The microcomputer-based control and timing system 102 comprises a data and control bus 140 that interconnects the components of system 102 with self-timed logic DSPs 152–168, also denoted DSP1–DSPn, of physiologic input signal processing circuit 108 and with any other ICs of the IMD 100. The DSPs 152–168, depicted in greater detail in FIG. 6, receive signals from the microcomputer-based control and timing system 102 on the data and control bus 140, process analog physiologic input signals, and provide digitized output signals on the data and control bus 140 to the components of the microcomputer-based control and timing system 102. The microcomputer-based control and timing system 102 also comprises a self-timed logic microprocessor 142, memory circuit 144, on-chip self-timed I/O signal processing logic block 146, on-chip self-timed logic block 148, and clocked timers 150 coupled together by the data and control bus 140.

The on-chip self-timed I/O signal logic block 146 generates the patient alert trigger signals delivered to the patient alert driver circuit 118 and processes the RS signal generated by reed switch circuit 120 and ERI signal generated by a battery voltage monitor circuit in power supply/POR circuit block 126. The on-chip self-timed I/O signal processing logic block 146 also provides timing control of data flow on data and control bus 140. The on-chip self-timed I/O signal processing logic block 146 also can include certain uplink and downlink telemetry signal processing stages. For example, the downlink telemetry signal may be processed by a DSP of the type depicted in FIG. 6 and described below located in on-chip, self-timed I/O signal processing logic 146 to differentiate legitimate downlink telemetry signals from EMI and noise, e.g., signals emitted by theft detectors. Other inputs and outputs that are not time dependent, i.e., do not require timing out a time period, can be generated by self-timed I/O signal processing logic block 146. The on-chip, self-timed I/O signal processing logic block 146 may, however, be prompted to provide an output or process an input by an output of a clocked timer 150.

The on-chip self-timed logic block 148 can include data management and computation circuits typically associated with the microprocessor based systems and data buses, including, for example, a direct memory address (DMA) controller, a block mover/reader, and a cyclic redundancy code (CRC) calculator. The on-chip, self-timed logic block 148 may also include circuits that are prompted to provide an output or process an input by an output of a clocked timer 150.

The clocked logic timers 150 can time out time periods that are started by a trigger signal received from the on-chip self-timed logic blocks 146 and 148 or the DSPs 152–168. The clocked logic timers 150 may also include a real time clock to append date and time stamp data to data stored in RAM in memory 144 or to trigger certain daily tests and operations, e.g. stimulation threshold tests, battery voltage tests and the like.

The IMD 100 of FIG. 1, incorporating the microcomputer-based timing and control system 102 and physiologic input signal processing circuit 108 of FIG. 2 can be configured to operate as a pacing system as described in detail below or as an ICD, brain stimulator or other nerve, organ or muscle stimulator, and is particularly useful where a multitude of sensors or sense electrode pairs are employed in the system. For example, multiple sensing and stimulation electrodes can be employed in bladder stimulation, deep brain stimulation or diaphragm stimulation.

At least two self-timed logic schemes have been devised in recent years that differ from conventional clocked Boolean logic in a variety of ways. Fundamentally, self-timed logic elements, like clocked Boolean logic elements, have at least one and typically two or more inputs and an output and provide an output level that may or may not be changed when an input level changes pursuant to governing logic rules of the particular element and any other input signal levels. Clocked Boolean logic elements process the input level change in timed relation to a clock signal occurring after the input level change. Self-timed logic responds to and propagates an input level change without the delay attendant to awaiting a clock signal. The output level of a self-timed logic element changes after a self-propagation time, if change is dictated by the applicable rules and the other input levels. Thus, in a self-timed logic circuit formed of a plurality of self-timed logic elements, data flow propagates from the circuit input to the circuit output through the logic elements (sometimes referred to as nodes or cells) analogous to following a flow chart. The processing of a change in an input signal level or state takes as much time as is necessary, not one or more clock cycles, to sequentially traverse the chain of self-timed logic elements to the output and to resume a state of readiness to accept and process a succeeding change in an input signal level. Within such a self-timed logic circuit, the power consumption due to clock energy dissipation is obviously eliminated, and residual ground or substrate noise level is also reduced by the absence of the clock signal.

Delay insensitive data encoding, referred to as Null Convention Logic™ (NCL) has been developed by Theseus Logic Inc., Orlando, Fla., and described in a number of publications and in U.S. Pat. No. 5,350,463 and a subsequently issued series of related patents. The fundamental NCL cell or element 300 depicted in FIG. 3 features three logic states, True(1), False(0) and Null, and a feedback loop and is devised as an M-of-N threshold gate with hysteresis that processes a DATA(1) and DATA(2) input level. In CMOS implementation, DATA is represented by a "high" level, e.g., $V_{DD}$ and NULL is a "low" level or ground. The output of a fundamental NCL cell or element 300 is maintained at its current state through hysteresis, and a new output cannot be asserted until a complete set of DATA input levels are present at M-of-N inputs. When the output asserts DATA, it will not change to NULL until all N inputs are NULL. These characteristics of a circuit devised of NCL cells or elements are represented to define a symbolically complete logic which is self-timed and independent of the propagation delays of its component cells or elements at the logic level. Consequently, a circuit formed of fundamental NCL cells or elements does not experience "racing" or exhibit spurious outputs.

The mathematical expressions and theory of NCL and its implementation in two value logic for a variety of gates, flip-flops, and the like, are set forth by Fant et al. in "NULL Convention Logic™" (Theseus Logic, Inc., 1997, 35 pp.), by Wang et al. in "Technology Independent Design Using NULL Convention Logic™" (Theseus Logic, inc., Oct. 19, 1998 19 pp.), and in the above-referenced '463 patent and other patents assigned to Theseus Logic, Inc. The design and fabrication of NCL building blocks, e.g. DSPs, logic circuits, timers, and high speed micro-processor cores, have been announced by Theseus Logic, Inc. and partners including Sanders Associates, Motorola, Inc., and the Defense Advanced Research Projects Agency (DARPA) as reported at http://www.sanders.com/hpc/cl/overview.html.

A self-timed control logic design 400 advanced by Cogency Technology, Inc., Toronto, Ontario, CANADA, and illustrated in FIG. 4 advances data through a self-timed circuit that comprises a sequence of data handling stages each stage, e.g., stage "n", comprising a flip-flop or latch 402 for storing a data level, a latch-controller 404, and a delay matching element 406. Incoming data from an upstream input source or a upstream stage is accompanied by a request (REQ) directed to the latch-controller of the receiving stage.

The latch-controller of the receiving stage responds to the REQ with an acknowledgment (ACK) sent to the upstream latch-controller, and stores the incoming bundled DATA in the flip-flop or latch of the receiving stage. The delay matching element at the output of the latch of each stage simply delays the control signals long enough for the combinational logic functions on the data path to settle. The REQ, ACK, and DATA together are called a "channel", and the above described communication over a channel is called a "handshake". See "Introduction to Self-Timed Design" (Cogency Technology, @ http//:www.cogency.co.uk/tech/index.html, © 1999, 8 pp.)

These publicized efforts are directed at development of self-timed logic microprocessors and circuit building blocks that operate at high speed comparable to 500 MHz or greater clock speeds and to reduce or eliminate the consumption of such high speed clock power and its dissipation as heat in relatively large scale computing systems. Such computational power and speed are not necessary for the IMD applications described above in reference to FIG. 1, and heat dissipation is not an issue in relatively low speed IMD data flow, computations and timing as described above.

However, the reduction in power caused by elimination of the clock is important for limiting energy consumption by the limited capacity, low voltage batteries employed in IMDs. And minimizing the clock tree frees up IC chip real estate to accommodate additional circuitry. Moreover, self-timed logic circuitry can operate reliably over a broader range of $V_{DD}$ and is less sensitive to IC process changes than clocked logic. Supply voltage lowers in IMDs as battery depletion occurs which can cause clocked logic circuits to be come unreliable, whereas self-timed logic circuits simply slow incrementally as supply voltage decreases but operate well within timing constraints in which IMD functions have to be performed. IC process changes that affect the sequence of clocked logic operations and can cause clock timing conflicts are readily implemented in self-timed logic circuits.

Implantable cardiac pacing systems incorporated into pacemaker IPGs or as part of ICD IPGs have become increasingly more complex in design and in functional operation as described below in reference to FIG. 5. Clocked logic circuits are affected by clock skew and race conditions which become more severe as the clock tree extends to ever increasing numbers of switched logic elements on a given IC or on separate ICs. A great deal of design time, effort, and expense must be expended in timing analysis, worst case timing simulations, etc., of a given IC layout to arrive at a final IC layout that minimizes these adverse conditions.

FIG. 5 is a detailed block diagram of the microcomputer-based control and timing system and physiologic input signal processing circuit of FIG. 1 for a multi-chamber pacing system of the type described, for example, in commonly assigned U.S. Pat. No. 5,902,324 which can be implemented into a pacemaker IPG or into an ICD to provide pacing functions. In such multi-chamber pacing systems that have been disclosed in the prior art, pacing and sensing electrodes are distributed in relation to two, three or four heart chambers to provide pacing and sensing functions. Hybrid analog and digital sense amplifiers are coupled to selected electrode pairs for sensing characteristic cardiac signals of the PQRST electrogram originating in or traversing the heart chamber, and sense event signals are generated by the sense amplifiers when detection criteria tailored to the characteristic cardiac signals are satisfied. The sense event signals are treated as trigger or reset signals to start or terminate a timed period governed by the pacing operating algorithm. Complex operating algorithms for three and four chamber pacing systems are set forth in the above-referenced '324 patent and in commonly assigned, co-pending U.S. patent application Ser. No. 09,1439,244 filed Nov. 12, 1999, for MULTI-SITE CARDIAC PACING SYSTEM HAVING CONDITIONAL REFRACTORY PERIOD.

In addition, further analog sense amplifiers are provided for providing EGM signals that are digitized by an ADC and then stored in RAM as episode data for uplink data transmission to the external programmer as described above in reference to FIG. 1. Such conventional, prior art, sense amplifiers have become increasingly more complex as they are called upon to distinguish characteristics of interest in the cardiac signals in each of the heart chambers or in multi-site sensing in the same heart chamber. In a four chamber pacing system, separate sense amplifiers or a multiplexed sense amplifier are coupled to each selected pair of sense electrodes distributed about the heart.

These problems and concerns can be alleviated through the selective use of self-timed logic DSPs in lieu of conventional analog and digital clocked logic circuits. FIG. 5 depicts a four chamber pacing system employing electrode pairs that would be selected for the right atrium (RA), left atrium (LA), right ventricle (RV) and left ventricle (LV) from which characteristic electrical signals of interest originating in or traversing each such chamber would be detected by a DSP. Moreover, the near field or far field EGM would be sampled and processed by further DSPs coupled with selected bipolar or unipolar sense electrodes, respectively, for event or episode related EGM data storage. The DSPs performing EGM signal processing would have differing gain, filtering and signal processing characteristics than DSPs performing event detection, but some or all of the sense electrode pairs in the four chambers could be employed for both EGM signal processing and event detection. Thus, for example, the RA, LA, RV and LV sense electrode pairs are coupled to the inputs of self-timed logic DSP3, DSP4, DSP5 and DSP6, and selected pairs of far field and near field EGM sense electrodes are coupled to the inputs of self-timed logic DSP7 and DSP8.

In addition, the output signals of physiologic sensors are coupled to the inputs of self-timed logic DSP1 and DSP2. One or more physiologic sensor can be employed to derive signals reflecting the need for cardiac output experienced by a patient to adjust the pacing rate, and timing and sequence of delivery of pacing pulses to the right and left atria and ventricles. One such physiologic sensor may comprise an activity sensor mounted to the housing of the pacing system IPG, and another sensor may comprise a blood gas, blood pressure, temperature, minute ventilation (MV) or pH sensor. The output signals of such sensors are processed and combined in a pacing rate setting algorithm as disclosed, for example, in commonly assigned U.S. Pat. Nos. 5,282,839 and 5,562,711, for example, to derive an optimum pacing rate.

The substitution of clocked logic DSPs for such complex sense amplifiers and also for circuits that process output signals of physiologic sensors is set forth in commonly assigned, co-pending U.S. patent application Ser. No. 09/399,318 filed Sep. 20, 1999, for CARDIAC PACING SYSTEM WITH IMPROVED PHYSIOLOGIC EVENT CLASSIFICATION AND HEART MONITORING BASED ON DSP and Ser. No. 09/181,460, filed Oct. 28, 1998, for POWER SUPPLY REDUCTION IN MEDICAL DEVICES USING MULTIPLE SUPPLY VOLTAGES AND CLOCK FREQUENCY CONTROL. The principles of operation of such DSPs remain the same whether they are implemented in clocked logic or self-timed logic of the types disclosed in FIGS. 3 and 4 and described above. However, there is no need to rely upon a universal clock for operating the DSPs implemented in self-timed logic.

FIG. 6 illustrates the principal blocks of a DSP IC 50 integrated with a first stage analog amplifier and filter 62 having a filter characteristic of about 0.7 to 500 Hz, for example. The DSP IC 50 includes an ADC 64 for performing A/D conversion, a digital filter block 65, a sense block 66 and a form analysis block 68 coupled to program registers 75 and I/O interface 70 and a local bus 72 coupled to data and control bus 140 of FIGS. 2 and 5. The general principles of operation of a DSP implemented in self-timed logic are disclosed, for example, in the article by Jacobs et al., entitled "A Fully Asynchronous Digital Signal Processor Using Self-Timed Circuits", *IEEE Journal of Solid-State Circuits*, vol. 25, no. 6, 12/90, pp. 1526–1536.

The amplified and filtered analog input signal is processed by ADC 64 to generate a digital output signal at a predetermined sampling frequency, e.g., 256 or 512 samples per second for cardiac signals. The ADC 64 can be clocked at the selected sampling frequency by way of an on-board local oscillator or can be implemented in self-timed logic as disclosed, for example, in U.S. Pat. No. 5,014,057.

The DSP1–DSPn IC 50 depicted in FIG. 6 provides analog-to-digital conversion of the physiologic signal provided by said sensing means and signal processing of the digitized physiologic signals input thereto as shown in FIGS. 2 and 5 to provide processed output signals to bus 140. Specifically, the output signals of physiologic sensors of the types described above can be sampled, digitized and processed by DSP1 and DSP2 and the far field and near field EGM can be sampled, digitized and processed by DSP7 and DSP8 in FIG. 5. Moreover, the digitized physiologic input signals can be processed in DSP1–DSPn of FIG. 2 with reference to event detection criteria or other predetermined discrimination criteria for determining the presence or absence of a predefined characteristic of the physiologic signal and providing a sense event signal upon determination of the pre-defined characteristic. Specifically, the cardiac signals conducted from the sense electrode pairs coupled to the inputs of DSP3–DSP5 of FIG. 5 can be digitized, processed and compared to specified P-wave, R-wave and T-wave detection criteria appropriate to each electrode site to provide accurate sense event output signals in FIG. 5.

The ADC 64 is suitably a delta-sigma modulator followed by a decimeter to provide typically 8-bit bytes at the chosen sampling interval. The bytes that are outputted from ADC 64 are then applied to digital filter 65 which is suitably a digital bandpass filter having a characteristic to remove high frequency artifacts, low frequency signal components, and the offset of the ADC 64. The filtered byte signal SIG output from digital filter 65 are applied to sense block 66. Sense block 66 obtains the slew rate, or slope SL, of the digitized and digitally filtered signal SIG corresponding to an event that is to be classified. The slope signals SL are processed with the SIG signal by form analysis block 68. In the case of a sense amplifier function performed by DSP IC 50, form analysis block 68 provides a sense event output to bus 140 if and when sense event criteria are satisfied by the SIG and SL signals. The detailed description of the operation of the sense block 66 and form analysis block 68 appears in the above-referenced '318 application.

The signal processing characteristics of each ADC 64, digital filter 65, sense block 66, and form analysis block 68 of each DSP1–DSPn IC 50 can be specifically tailored in program registers 75 to provide optimal event detection of a specific input signal characteristic or processing of the input signal for accuracy and fidelity. The sampled byte signal processing through these components downstream of ADC 64 proceeds at the propagation speed allowed by the self-timed logic element chain, and can be readily accomplished in the sample periods between each A/D conversion by ADC 64.

The microcomputer timing and control system 102 responds to cardiac sense event signals generated in FIG. 5, by DSP3–DSP7 in a variety of ways. Certain nonrefractory sense events terminate time-out of pacing escape intervals and delay intervals being timed out by clocked logic timer block 150 as described further below. The timing and sequences of particular cardiac sense event signals are subjected to rate and pattern criteria to determine, for example, whether a tachyarrhythmia condition exists and to counter or ameliorate its effects by mode switching, rate stabilization, and the like. In addition, storage of the EGM signals output by DSP7 and DSP8 and physiologic sensor signals output by DSP1 and DSP2 in memory locations of RAM in memory 144 may be commenced. In this way, episode data may be stored for later retrieval and uplink telemetry to the external programmer 110.

The programmable escape interval is preferably timed out by a clocked timer 150 that times out the programmed escape interval as multiples of the crystal oscillator generated clock interval. The self-timed logic microprocessor 142 responds to interrupts, e.g., a sense event signal or sensor output by a DSP, or time-out of the escape interval and other time periods, or receipt of a downlink telemetered signal or the like. The self-timed logic microprocessor 142 performs the functions of controlling operating mode per the programmed-in operating mode and applies programmed operating parameter values, e.g., the programmed pacing escape interval, AV delay, and post-atrial and post-ventricular delays, at its own propagation speed upon receiving an interrupt and then returns to a dormant state.

The number n of DSPs employed in the pacing system of FIG. 5 depends on how it is to be employed in a particular pacemaker IPG or ICD IPG. The multi-chamber pacing system depicted in FIG. 5 is particularly directed to pacing diseased hearts having conduction defects and/or in congestive heart failure (CHF). In CHF, cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

A number of proposals have been advanced for providing pacing therapies to alleviate these conditions and restore synchronous depolarization and contraction of a single heart chamber or right and left, upper and lower, heart chambers as described in detail in the above-referenced '324 patent and '244 patent application, for example.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at least one of the electrode sites. It is believed that atrial and left ventricular cardiac output can be significantly improved when left and right chamber synchrony is restored through either simultaneous delivery or specified sequences of delivery of right and left heart chamber pacing pulses, particularly in patients suffering from dilated cardiomyopathy and CHF. In cases involving conduction defects of a single heart chamber, it is believed that an improvement in cardiac output can be achieved by locating pace/sense electrodes at specific sites of the single heart chamber and pacing all sites simultaneously or in particular order, depending upon the site where a sense event is first detected during time-out of a pacing escape interval.

In bi-chamber (bi-atrial or bi-ventricular) pacemakers, pacing pulses are delivered to one or the other or both of the right and left heart chambers upon expiration of a pacing escape interval. The escape interval is restarted upon delivery of a pacing pulse or upon a non-refractory right or left heart chamber sense event. Post-event time periods are started upon delivery of a pacing pulse or upon a refractory or non-refractory sense event. The delayed right-to-left or left-to-right conduction of an evoked depolarization resulting from delivery of a pacing pulse to the right or left heart chamber, respectively, and capture of that heart chamber traverses the non-paced pace/sense electrode after a delay that enables it to be sensed and mistakenly characterized as a refractory sense event. Here also, a second restarting of post-event time periods due to a mistakenly characterized refractory sense event can result in the failure to respond appropriately to the next true, spontaneous sense event in either of the right and left heart chambers. Thus, the timing of delivery of bi-atrial or bi-ventricular pacing pulses can also be disrupted.

Similar problems arise in AV sequential, bi-atrial and/or bi-ventricular pacing systems, wherein three or four heart chambers are paced and sensed. A V-A pacing escape interval is typically restarted by one of the following events: delivery of a ventricular pacing pulse at the time-out of an AV delay to one of the right or left or to both ventricles; a spontaneous, non-refractory, ventricular sense event sensed in one ventricle before the time-out of the AV delay; or a spontaneous, non-refractory, ventricular sense event sensed in one ventricle before the time-out of the V-A escape interval and typically after time-out of an upper rate interval (URI) that defines the maximum pacing rate. A set of post-ventricular event timers are started upon each such event and time out post-ventricular event periods, e.g. atrial and ventricular blanking periods and refractory periods and the URI. The post-ventricular event timers start a ventricular refractory period (VRP) and at least one post-ventricular event period that affects the treatment of an atrial sense event occurring during its time-out. For example, an atrial sense event occurring during the time-out of a post-ventricular atrial refractory period (PVARP) can be ignored for purposes of resetting the V-A escape interval and starting the AV delay. The PVARP is typically programmable and can be set to prevent any response to an atrial sense event that may be caused by sensing of the antegrade conduction of the spontaneous or evoked ventricular depolarization through the atria and to the atrial pace/sense electrodes. The PVARP, VRP and URI interval are restarted each time that a ventricular pacing pulse is delivered and whenever a refractory or non-refractory ventricular sense event occurs.

The V-A delay is also terminated by its time-out and delivery of the programmed atrial pace pulse or pulses or a non-refractory atrial sense event. An atrial refractory period (ARP) and an AV delay interval are commenced upon termination of the V-A escape interval. A single ventricular pace pulse or right and left ventricular pacing pulses are delivered at expiration of the AV delay interval or the AV delay interval is terminated by a non-refractory ventricular sense event detected before its time-out. The V-A escape interval is then restarted.

The delivery of pacing pulses to right and left heart atria and ventricles upon expiration of the AV delay and V-A escape interval, respectively, is governed by programmed sequence, which may be simultaneous or with a right-to-left or left-to-right delay and either be committed or inhibited by a sense event detected in the second chamber to be paced prior to time out of the delay. A similar operation is effected for multi-site pacing and sensing at spaced apart pace/sense electrode sites in a single atrial and/or ventricular heart chamber.

Problems surface in implementing multi-site pacing in a single heart chamber or in right and left heart chamber pacing within the contexts of conventional timing and control systems for characterizing and responding to sense event signals generated by sense amplifiers coupled to spaced apart pace/sense electrodes. Inappropriate responses can be triggered by depolarizations conducted between the separated pace/sense electrode sites and sensed by sense amplifiers coupled to those pace/sense electrodes which upset the timing of delivery of subsequent pacing pulses. In right and left heart pacing systems, pacing and sensing problems arise when right-to-left or left-to-right conduction delays vary depending on right and left ventricle pace/sense electrode placement, transient conditions of the heart, and chronic CHF.

The above-described pacing system of FIG. 5 can be tailored as such a bi-chamber pacing system for two, three or four chambers or as a multi-site single chamber pacing system wherein the DSPs that are utilized are tuned to accurately distinguish true refractory and non-refractory sense events and spontaneous and conducted sense events at each electrode site in a single heart chamber or the right and left heart chambers.

Although the preferred embodiment of a pacing system in which the present invention is described above is relatively complex, it will be understood that the same allocation of clocked and self-timed logic can be provided in less complex pacing systems, e.g., atrial or ventricular single chamber pacing system that typically functions in an AAI or AAIR mode or VVI or VVIR mode, respectively, or a conventional AV sequential pacing system functioning in the DDD or DDDR mode.

The fabrication of clocked and self-timed logic in a single IC in the IMD operating system architectures of the present invention is compatible with various fabrication technologies such as silicon on insulator (SOI), silicon on sapphire (SOS) CMOS technologies as well as conventional silicon CMOS technologies. The present invention as described herein is enabling technology for the use of DSPs to perform more functions due to the manner in which power consumption can be reduced for such DSPs.

As the power consumption and space for clock trees are reduced, further functionality can be added to IMDs in accordance with the present invention. For example, additional self-timed logic DSPs may perform various morphology detection functions such as differentiation of retrograde P-waves and antegrade P-waves of EGM waveform; differentiation of P-waves from far field R-waves; differentiation of atrial fibrillation, atrial flutter and atrial tachycardia from sinus tachycardia; differentiation of ventricular fibrillation and ventricular tachycardia from SVT; differentiation of cardiac signals from electromagnetic interference, etc.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. An implantable medical device for at least one of delivering a therapy to a patient's body and monitoring a physiologic condition of a patient comprising:
    a battery to provide battery energy; and
    at least one integrated circuit powered by the battery and providing control and timing functions, said integrated circuit including:
        (a) a system clock providing clock signals;
        (b) clocked logic circuits responsive to said clock signals to perform defined circuit functions in timed synchrony with said clock signals;
        (c) a clock tree that couples said clock signals from said system clock to the clocked logic circuits;
        (d) means for sensing a physiologic condition of the patient and providing a physiologic signal; and
        (e) at least one self-timed logic circuit operating independent of said system clock to process the physiologic signal, whereby the clock tree is minimized and clock energy is conserved; said self-timed logic circuit comprising a signal processor having a plurality of self-timed logic elements formed into a chain, the signal processor receiving the physiologic signal at an input thereof, processing the physiologic signal, and providing the processed physiologic signal at an output after a self-timed logic propagation delay.

2. The implantable medical device of claim 1, wherein the signal processor comprises a digital signal processor that provides analog-to-digital conversion of the physiologic signal provided by said sensing means and signal processing of the digitized physiologic signal.

3. The implantable medical device of claim 1, wherein the signal processor comprises a digital signal processor that provides analog-to-digital conversion of the physiologic signal, forms a digitized physiologic signal, processes the digitized physiologic signal with reference to predetermined discrimination criteria, determines the presence or absence of a predefined characteristic of the physiologic signal, and provides a sense event signal upon determination of the predefined characteristic.

4. The implantable medical device of claim 3, wherein:
    said clocked logic circuits comprise at least one timer that times out time periods as multiples of the clock time period in response to a sense event signal; and further comprising:
    means responsive to time-out of a time period by said timer for performing a first device operation; and
    means responsive to a sense event signal provided during time-out of a time period for performing a second device operation.

5. The implantable medical device of claim 1, wherein said self-timed logic circuit further comprises:
    a microprocessor, a timing and control bus, and RAM/ROM memory to store data and instruction sets implementing device operation algorithms.

6. An implantable cardiac pacing system for sensing cardiac signals and delivering pacing pulses through pace/sense electrodes situated in one or more heart chambers comprising:
    a battery to provide battery energy; and
    at least one integrated circuit powered by the battery and providing control and timing functions, said integrated circuit including:
        (a) a system clock providing clock signals;
        (b) a clocked logic circuit responsive to a clock signal to time-out a pacing escape interval;
        (c) means responsive to time-out of the pacing escape interval for generating and delivering a pacing pulse to the pace/sense electrodes;
        (d) a clock tree that couples said clock signals from said system clock to the clocked logic circuit;
        (e) means coupled with said pace/sense electrodes for sensing a cardiac signal of the patient and providing a cardiac sensed event signal; and
        (f) at least one self-timed logic circuit operating independent of said system clock to process the sensed event signal, whereby the clock tree is minimized and clock energy is conserved; said self-timed logic circuit comprising a signal processor coupled with said cardiac signal sensing means and having a plurality of self-timed logic elements formed into a chain, the signal processor receiving the cardiac sensed event signal at an input thereof, processing the cardiac sensed event signal, and providing the processed cardiac sensed event signal at an output after a self-timed logic propagation delay.

7. The implantable pacing system of claim 6, wherein the signal processor comprises a digital signal processor that provides analog-to-digital conversion of the cardiac signal and processes the digitized physiologic signal.

8. The implantable pacing system of claim 6, wherein the signal processor comprises a digital signal processor that provides analog-to-digital conversion of the cardiac signal, processes the digitized cardiac signal with reference to predetermined discrimination criteria, determines the presence or absence of a predefined characteristic of the cardiac signal, and provides a sense event signal upon determination of the pre-defined characteristic.

9. The implantable pacing system of claim 8, further comprising:
    means for restarting the time-out of the pacing escape interval in response to a sense event signal.

10. The implantable pacing system of claim 6, wherein said self-timed logic further comprises:
    a memory having a plurality of memory locations; and
    means for triggering storage of said processed cardiac signal in the plurality of memory locations.

11. The implantable pacing system of claim 6, wherein said self-timed logic circuit further comprises a microcomputer, a timing and control bus, and RAM/ROM memory that stores data and instruction sets of device operation algorithms, the microcomputer operating pursuant to the stored data and operating instruction sets to establish timed out time periods and perform pacing pulse delivery and to adjust sensing criteria for sensing cardiac events.

* * * * *